United States Patent
Kanikanti et al.

(10) Patent No.: US 6,569,455 B1
(45) Date of Patent: May 27, 2003

(54) QUICK-RELEASE EXTRUDATES, METHOD FOR PREPARING THE SAME AND COMPOSITIONS OBTAINED FROM SAID EXTRUDATES

(75) Inventors: Venkata-Rangarao Kanikanti, Leverkusen (DE); Jürgen Sdebik, Düsseldorf (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/031,129

(22) PCT Filed: Jul. 12, 2000

(86) PCT No.: PCT/EP00/06584

§ 371 (c)(1),
(2), (4) Date: Jan. 9, 2002

(87) PCT Pub. No.: WO01/07015

PCT Pub. Date: Feb. 1, 2001

(30) Foreign Application Priority Data

Jul. 23, 1999 (DE) .......................................... 199 34 610

(51) Int. Cl.⁷ ............................. A61K 9/20; A61K 9/48; A61K 9/62; A61K 9/26; A61K 9/36
(52) U.S. Cl. ...................... 424/464; 424/451; 424/452; 424/461; 424/465; 424/469; 424/479; 424/480
(58) Field of Search ................................ 424/451, 464, 424/465, 452, 461, 469, 479, 480, 489, 499

(56) References Cited

U.S. PATENT DOCUMENTS

| | | | | |
|---|---|---|---|---|
| 4,317,447 A | | 3/1982 | Williams | 128/260 |
| 5,039,699 A | * | 8/1991 | Kurihara et al. | 514/458 |
| 5,641,516 A | | 6/1997 | Grabowski et al. | 424/489 |
| 5,939,099 A | * | 8/1999 | Grabowski et al. | 424/488 |
| 6,399,100 B1 | * | 6/2002 | Clancy et al. | 424/468 |

FOREIGN PATENT DOCUMENTS

| | | | |
|---|---|---|---|
| DE | 19536387 | | 3/1997 |
| EP | 0596203 | | 5/1994 |
| EP | 0864326 | | 9/1998 |
| WO | 9318755 | | 9/1993 |
| WO | WO 96/25149 | * | 8/1996 |
| WO | 9625151 | | 8/1996 |

OTHER PUBLICATIONS

Chang, R., "A Comparison of Rheological and Enteric Properties among Organic Solutions, Ammonium Salt Aqueous Solutions, and Latex systems of Some Enteric Polymers", Pharma. Tech. , 62–70 (1990).

* cited by examiner

Primary Examiner—Thurman K. Page
Assistant Examiner—S. Tran
(74) Attorney, Agent, or Firm—Susan M. Pellegrino

(57) ABSTRACT

The present invention relates to stable quick-release extrudates that contain low-viscosity hydroxypropylcellulose and at least one active ingredient. This invention also relates to a method for preparing said extrudates without the use of solvents as well as to the use of said extrudates in the production of quick-release preparations.

9 Claims, No Drawings

QUICK-RELEASE EXTRUDATES, METHOD FOR PREPARING THE SAME AND COMPOSITIONS OBTAINED FROM SAID EXTRUDATES

This application is a 371 of PCT/EP00/06584 filed Jul. 12, 2000.

The present invention relates to stable, fast-release melt extrudates comprising hydroxypropylcellulose of low viscosity and at least one active pharmaceutical ingredient and to a solvent-free process for their production, and to their use in the production of fast-release preparations.

Accurate control of release of active ingredients from preparations is of great pharmaceutical importance. In use besides slow-release preparations and those with controlled release are fast-release preparations which ensure a rapid rise in the level of the active ingredient in the circulation in an acute pathological state.

Extrusion processes are frequently used to produce corresponding preparations. The principle of melt extrusion has been known for a long time (Beckmann 1964). In the extrusion process, active ingredients and polymer are conveyed either simultaneously, without previous mixing, or as mixture, after previous mixing, in an extruder which has been heated so that the mixture becomes extrudable and the active ingredient is not degraded.

In contrast to conventional coprecipitate methods, the use of solvents is unnecessary in this case: this is particularly important because, besides the economic aspects, the use of solvents leads to special technical problems such as prevention of explosions in the premises and equipment.

The production of preparations with rapid release of active ingredient by melt extrusion of hydroxypropylcellulose (HPC) with a molecular weight of from 60 000 to 200 000 is described in the application WO 96/25149. The content of hydroxypropylcellulose in these preparations is from 10 to 30, preferably 20 to 30, % by weight.

Such low contents of polymer are disadvantageous from the pharmaceutical viewpoint because the resulting preparation is, especially on use of high-potency active ingredients, very small and thus difficult for the patient to handle, which considerably reduces patient compliance. Extending the preparation with fillers in turn increases the number of ingredients used and thus complicates the process. This is disadvantageous inter alia in relation to the compatibility of the fillers with the active ingredient in particular at elevated temperature during the extrusion.

A further disadvantage is the difficulty of maintaining content uniformity, i.e. the uniformity of the preparations in relation to the amounts of active ingredient.

One object of the present invention is to be regarded as being to provide fast-release, stable extrudates with good content uniformity and handleability for all types of active ingredients, in particular for slightly soluble active ingredients.

It has now been found, surprisingly, that transparent melt extrudates with the desired fast release and high stability can be obtained in a simple manner with the specifically selected polymer hydroxypropylcellulose of low viscosity with an average molecular weight of from 30 000 to 100 000 and with a molar degree of substitution of at least 3 in an amount of at least 50% by weight, preferably 66% by weight, based on the active ingredient/polymer mixture in conjunction with amorphous active ingredients.

The melt extrudates of the invention comprise hydroxypropylcellulose of low viscosity with an average molecular weight of from 30 000 to 100 000 and with a molar degree of substitution of at least 3 in an amount of at least 50% by weight, preferably 66% by weight, based on the active ingredient/polymer mixture, one or more active ingredients and, where appropriate, excipients.

Preferred melt extrudates comprise hydroxypropylcellulose in an amount of at least 66% by weight based on the active ingredient/polymer mixture.

The hydroxypropylcellulose preferably has an average molecular weight of from 55 000 to 70 000.

The molar degree of substitution refers to the average number of moles of propylene oxide reacted per glucose unit in the cellulose.

The present application also relates to preparations produced with use of the extrudates of the invention. Fast-release extrudates or preparations mean for the purposes of the invention those which release 80% of the active ingredient(s) within 60 min in the USP XXII paddle method. The extrudates or preparations of the invention display very rapid release and show a significant supersaturation. They are therefore particularly well suited for fast reaching of high plasma concentrations of active ingredient. The fast release can be controlled as required by varying the production parameters. The release of active ingredient is influenced, for example, by the concentration of active ingredient in the final product or by extrusion process parameters such as the screw geometry, the extrusion rate, the extrusion temperature, the diameter and surface area of the extrudate etc. The release rate is influenced in particular by the particle size of the extrudate. In single-unit dosage forms such as, for example, tablets, the release is influenced in particular by the content of disintegrant in the finished formulation.

Fast release, but at different times, of the active ingredient on oral administration can be achieved by coating the extrudates or preparations in such a way that they release the active ingredient only in a particular region of the gastrointestinal tract, for example with Eudragit L or S. Coatings of this type are dissolved, for example, specifically at particular pH values and make release possible at the optimal site. It is possible in this way, for example, to protect acid-sensitive active ingredients until the appropriate absorption window is reached (see in this connection Chang, R., Pharmaceutical Technology, October 1990).

It is also possible during the melt extrusion or during further processing, for example tableting, to use other conventional excipients which are conventional in pharmacy in the production of preparations and are known from the literature, such as, for example, magnesium stearate or masking flavors. None of these excipients is, however, necessary in order to achieve essentially the desired fast release of the drug.

In a preferred embodiment, the extrudate or the preparation is administered orally. For this purpose, in one embodiment, the extrudate of the invention is comminuted, for example ground to an average particle diameter of less than 0.5 mm, and packed into gelatin capsules or as sachets.

In a further embodiment, the extrudate of the invention is, where appropriate in comminuted form, mixed with a disintegrant and, where appropriate, further excipients and processed to a single-unit dosage form. Disintegrants are substances which ensure rapid disintegration of the single-unit dosage form in aqueous solution, such as, for example, crosslinked polyvinylpyrrolidone (PVPP). In this case it is preferred to use large amounts of disintegrant, that is to say more than 0.1 part by weight of disintegrant per 1 part of extrudate (active ingredient and HPC).

Single-unit dosage forms mean preparations which are administered as a single dose, for example tablets, coated tablets or capsules.

It is further possible in this way to produce combination products which comprise in a single-unit dosage form contents of different active ingredient-containing extrudates: thus, it is possible to use different active ingredients but also different extrudates differing in release profile in order to control accurately active ingredient contents in the circulation over time.

The active ingredient to be used may be any drugs such as, for example, antiinfectives, cardiovascular agents, antimycotics, antidepressants, antidementia agents, antiepileptics, antiinflammatory agents, analgesics, antiasthmatics, antithrombotics, antitumor agents, antimalarials, non-steroidal antiinflammatory drugs (NSAID), diuretics, antiarrhythmics, hypoglycemic agents, ACE inhibitors, sedatives, decongestants, antihistamines or lipid-lowering agents. Also suitable as active ingredients are crop protection agents or veterinary agents. For the purposes of the present invention, only those drugs which do not decompose under the temperature and processing conditions are incorporated. The amount of active ingredient to be administered per dosage unit may be varied within wide limits depending on the nature of the drug and the release rate. Slightly soluble active ingredients are preferred, that is to say those which have a solubility of less than 1 g/100–1 000 g of solvent. A further possibility is to employ mixtures of drugs.

The present invention further relates to a process for manufacturing the extrudates and preparations of the invention. This simple process requires only a conventional extruder and makes do without complicated manufacturing methods or solvents and plasticizers.

In the present process, a mixture of at least one active ingredient and hydroxypropylcellulose of low viscosity in an amount of at least 50% by weight, in particular at least 66% by weight, based on the active ingredient/polymer mixture and, where appropriate, further conventional pharmaceutical excipients is produced, and the mixture is passed through an extruder which has at the place where the product enters a temperature of from 20 to 40° C. and at the exit die or dies has a temperature of $\leq 225°$ C., where the exit dies have a diameter of from 0.5 to 5 mm, preferably from 1 to 3 mm, and the extruded strands are comminuted after their emergence. The residence time of the mixture in the extruder depends on technical aspects of the process and may vary to a large degree. It is generally less than 3 min, preferably less than 1 min.

The ingredients can be mixed before entry into the extruder or inside the latter. Premixing, that is to say mixing before entry, is preferred inter alia for reasons of the abovementioned content uniformity. Continuous operation of the extruder is likewise preferred.

It has been found, surprisingly, that extrusion is possible in the process of the invention even with large contents of hydroxypropylcellulose without the use of plasticizers or solvents. This was not to be expected by the skilled worker because in general an increasing content of hydroxypropylcellulose is associated with less good extrudability in a conventional extruder.

The viscosity is determined using a rotational viscometer in a known manner at 20° C. on a 2% strength aqueous solution; the low-viscosity celluloses of the present invention have viscosities of less than 400 cP.

The invention is explained further by means of the following examples.

EXEMPLARY EMBODIMENTS

Measurement of the Active Ingredient Release by the USP XXII Paddle Method

The release of the abovementioned active ingredients from the tablets or gelatin capsules is measured by the USP XXII paddle method. Stirrer speed 75 rpm, release medium 0.1 N HCl (0.9 l) with small amounts of solubilizers (for example: $\leq 0.5$ (w/v) sodium lauryl sulfate), temperature 37° C. All the examples of the invention apart from comparative example A release about 80% of active ingredient within 60 min.

Example 1

1 part by weight of nifedipine is mixed with 2 parts by weight of low-viscosity HPC (average MW 55 000–70 000). The mixture is processed in a twin screw extruder with an exit die having a diameter of 2 mm. The material is extruded at a die temperature of 170° C. The transparent extrudates are comminuted, and the fraction (<125 µm; 90 parts by weight) is mixed with 119 parts by weight of crosslinked polyvinylpyrrolidones (PVPP) and then with magnesium stearate (1 part by weight) and tableted (30 mg of nifedipine per tablet).

Example 2

1 part by weight of nifedipine is mixed with 2.5 parts by weight of low-viscosity HPC (average MW 55 000–70 000). The mixture is processed in a twin screw extruder with an exit die having a diameter of 2 mm. The material is extruded at a die temperature of 170° C. The transparent extrudates are comminuted, and the fraction (<125 µm; 105 parts by weight) is mixed with 135 parts by weight of crosslinked polyvinylpyrrolidones (PVPP) and then with magnesium stearate (1.2 parts by weight) and tableted (30 mg of nifedipine per tablet).

Example 3

Analogous to example 1 but the die temperature is 160° C.

Example 4

Analogous to example 1 but nimodipine is used as drug; the die temperature is 120° C.

Example 5

1 part by weight of 2-cyclopentyl-2-[4-(2,4-dimethylpyrido[2,3-b]indol-9-ylmethyl)phenyl]-N-(2-hydroxy-1-phenylethyl)acetamide is mixed with 2 parts by weight of low-viscosity HPC (average MW 55 000–70 000). The mixture is processed in a twin screw extruder with an exit die having a diameter of 2 mm. The material is extruded at a die temperature of 220° C. The transparent extrudates are comminuted, and the fraction (<125 µm; 240 parts by weight) is mixed with 118.8 parts by weight of crosslinked polyvinylpyrrolidones (PVPP) and then with magnesium stearate (1.2 parts by weight) and tableted (80 mg of (2S)-2-cyclopentyl -2-[4-(2,4-dimethylpyrido[2,3-b]indol-9-ylmethyl)phenyl]-N-(1R)-2- hydroxy -1-phenylethyl) acetamide per tablet).

Example 6

Analogous to example 1 but the mixture is packed into gelatin capsules.

Example 7

Analogous to example 4 but the mixture is packed into gelatin capsules.

Comparative Example A

Analogous to example 5 but 2 parts by weight of the drug 2-cyclopentyl-2-[4- (2,4-dimethylpyrido[2,3-b]indol-9- ylmethyl)phenyl]-N-(2-hydroxy-1-phenyl-1-phenyl-ethyl) acetamide are mixed with 1 part by weight of low-viscosity HPC (average MW 55 000–70 000). The mixture is processed in a twin screw extruder with an exit die having a diameter of 2 mm. The material is extruded at a die temperature of 220° C. The transparent extrudates are comminuted, and the fraction (<125 μm; 240 parts by weight) is mixed with 118.8 parts by weight of crosslinked polyvinylpyrrolidones (PVPP) and then with magnesium stearate (1.2 parts by weight) and tableted (80 mg of (2S)-2-cyclopentyl-2-[4-(2,4-dimethylpyrido[2,3-b]indol-9-ylmethyl)phenyl]-N-(1R)-2-hydroxy-1-phenylethyl) acetamide per tablet).

What is claimed is:

1. Stable, fast-release extrudates comprising hydroxypropylcellulose of low viscosity with an average molecular weight of from 30 000 to 100 000 and with a molar degree of substitution of at least 3 in an amount of at least 50% by weight based on the active ingredient/polymer mixture and at least one active pharmaceutical ingredient, wherein said fast-release extrudates releases 80% of the active ingredient within 60 minutes.

2. The extrudates as claimed in claim 1, characterized in that the extrudates comprise hydroxypropylcellulose in an amount of least 66% by weight based on the active ingredient/polymer mixture.

3. The extrudates as claimed in claim 1, characterized in that the extrudates comprise hydroxypropylcellulose with an average molecular weight of from 55 000 to 70 000.

4. A pharmaceutical preparation comprising the extrudates as claimed in any one of claims 1 to 3.

5. A pharmaceutical preparation as claimed in claim 4, characterized in that the preparation is a tablet which comprises the disintegrant crosslinked polyvinyl-pyrrolidone (PVPP).

6. A pharmaceutical preparation as claimed in claim 4, characterized in that the preparation is a sachet.

7. A pharmaceutical preparation as claimed in claim 4, characterized in that the preparation is a capsule.

8. A solvent-free process for producing extrudates as claimed in claim 1, characterized in that a mixture of at least one active ingredient and hydroxypropyl-cellulose of low viscosity in an amount of at least 50% by weight based on the active ingredient/polymer mixture is passed through an extruder which has at the place where the product enters a temperature of from 25 to 40° C. and at the exit die has a temperature of $\leq 225°$ C., where the exit die(s) has a diameter of from 0.5 to 5 mm, and the extruded strands are comminuted after their emergence.

9. The process as claimed in claim 8, characterized in that the exit die(s) has a diameter of from 1 to 3 mm.

* * * * *